United States Patent
Kobayashi

(10) Patent No.: US 9,898,839 B2
(45) Date of Patent: Feb. 20, 2018

(54) MEDICAL IMAGE DIAGNOSIS APPARATUS AND MAMMOGRAPHY APPARATUS

(71) Applicant: TOSHIBA MEDICAL SYSTEMS CORPORATION, Otawara-Shi (JP)

(72) Inventor: Yoshimasa Kobayashi, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 141 days.

(21) Appl. No.: 14/661,183

(22) Filed: Mar. 18, 2015

(65) Prior Publication Data

US 2015/0269766 A1    Sep. 24, 2015

(30) Foreign Application Priority Data

Mar. 19, 2014  (JP) ................ 2014-057191

(51) Int. Cl.
*G06T 11/00* (2006.01)
*A61B 6/00* (2006.01)
(Continued)

(52) U.S. Cl.
CPC ............ *G06T 11/003* (2013.01); *A61B 6/025* (2013.01); *A61B 6/469* (2013.01); *A61B 6/502* (2013.01);
(Continued)

(58) Field of Classification Search
None
See application file for complete search history.

(56) References Cited

U.S. PATENT DOCUMENTS 6,785,410 B2*  8/2004  Vining .............. G06F 17/30256
                                                      382/128
2007/0293752 A1* 12/2007  Simpkin ............. A61B 5/0091
                                                      600/407
2012/0300899 A1  11/2012  Tajima

FOREIGN PATENT DOCUMENTS

JP    09-212633 A    8/1997
JP    2006-340939 A   12/2006
(Continued)

OTHER PUBLICATIONS

Office Action dated Sep. 26, 2017, in Japanese Patent Application No. 2014-057191, filed Mar. 19, 2014.

*Primary Examiner* — Said Broome
(74) *Attorney, Agent, or Firm* — Oblon, McClelland, Maier & Neustadt, L.L.P.

(57) ABSTRACT

A medical image diagnosis apparatus emits radiation to a breast as a subject, detects radiation that has passed through the subject, and generates three-dimensional image data including a plurality of tomographic images of the subject. The medical image diagnosis apparatus includes an image generator, a setting unit, an image detector, and a display controller. The image generator projects the three-dimensional image data in a predetermined direction to generate a two-dimensional image. The setting unit sets a region of interest in the two-dimensional image. Based on the region of interest and a corresponding region that corresponds to the region of interest in each of the tomographic images, the image detector detects a tomographic image including the corresponding region that is similar in pixel value to the region of interest from the three-dimensional image data. The display controller displays the tomographic image detected by the image detector on a display unit.

9 Claims, 9 Drawing Sheets

(51) Int. Cl.
*A61B 6/02* (2006.01)
*G06T 15/08* (2011.01)
(52) U.S. Cl.
CPC .......... *A61B 6/5205* (2013.01); *A61B 6/5223* (2013.01); *G06T 11/006* (2013.01); *G06T 15/08* (2013.01); *A61B 6/466* (2013.01); *G06T 2211/436* (2013.01)

(56) References Cited

FOREIGN PATENT DOCUMENTS

| | | |
|---|---|---|
| JP | 2008-068032 A | 3/2008 |
| JP | 2012-245060 A | 12/2012 |
| JP | 2013-230404 A | 11/2013 |
| WO | WO 2005/011499 A1 | 2/2005 |

* cited by examiner

MEDICAL IMAGE DIAGNOSIS APPARATUS AND MAMMOGRAPHY APPARATUS

CROSS-REFERENCE TO RELATED APPLICATION

This application is based upon and claims the benefit of priority from Japanese Patent Application No. 2014-057191, filed Mar. 19, 2014; the entire contents of which are incorporated herein by reference.

FIELD

Embodiments described herein relate generally to a medical image diagnosis apparatus and a mammography apparatus.

BACKGROUND

X-ray diagnosis apparatuses, X-ray CT (computed tomography) systems, and mammography apparatuses are known as medical image diagnosis apparatuses for capturing an image of a subject.

For example, a mammography apparatus is used to acquire breast images of a subject. The breast images are interpreted and used to determine the presence of lesions such as breast cancer. In recent years, the rate of breast cancer has steadily been increasing, which has raised demand for early detection of lesions such as breast cancer.

The breast images include two-dimensional (2D) images (common mammography images) that contain layers of information in the thickness direction of the breast. Such 2D image is interpreted by a radiographic interpreter such as a radiologist. However, it is difficult to detect a lesion that overlaps with the mammary gland in the thickness direction of the breast.

Tomosynthesis is an imaging technique to produce three-dimensional (3D) image data including a plurality of tomographic images of the breast as a subject with a mammography apparatus.

In tomosynthesis imaging, X-rays of the subject are taken at different angles by using a mammography apparatus having a moving X-ray tube and an X-ray detector that are located facing each other with the subject between them. Projection data acquired by multiple times of radiography are reconstructed to generate 3D image data including a plurality of tomographic images.

A biopsy is sometimes performed to collect the tissue of a lesion detected by interpretation of radiographs with a puncture needle. In the biopsy, it is required to check the 3D position of the lesion. Therefore, an operator such as a doctor or the like searches for a tomographic image that demonstrates the lesion while switching display images from one tomographic image to another, and acquires the lesion in the tomographic image and its sectional position to check the 3D position of the lesion. This may force the operator to spend a long time switching display images to find out the lesion.

There is a method for checking the 3D position of the lesion. In this method, the lesion is specified in a common mammography image. Then, image analysis is performed on the mammography image and 3D image data to detect a position corresponding to the lesion from the 3D image data. The method requires two types of photography for capturing the common mammography image and the 3D image data, resulting in an increase in the radiation exposure of the subject. Besides, since the common mammography image and the 3D image data have different noise, the image analysis may have low accuracy. In this case, the position is detected from the 3D image data with low accuracy, and therefore it is difficult to check the 3D position of the lesion.

DETAILED DESCRIPTION

In general, according to one embodiment, a medical image diagnosis apparatus emits radiation to a breast as a subject, detects radiation that has passed through the subject, and generates three-dimensional image data including a plurality of tomographic images of the subject. The medical image diagnosis apparatus includes an image generator, a setting unit, an image detector, and a display controller. The image generator projects the three-dimensional image data in a predetermined direction to generate a two-dimensional image. The setting unit sets a region of interest in the two-dimensional image. Based on the region of interest and a corresponding region that corresponds to the region of interest in each of the tomographic images, the image detector detects a tomographic image including the corresponding region that is similar in pixel value to the region of interest from the three-dimensional image data. The display controller displays the tomographic image detected by the image detector on a display unit.

First Embodiment

[Configuration]

Figure 1:
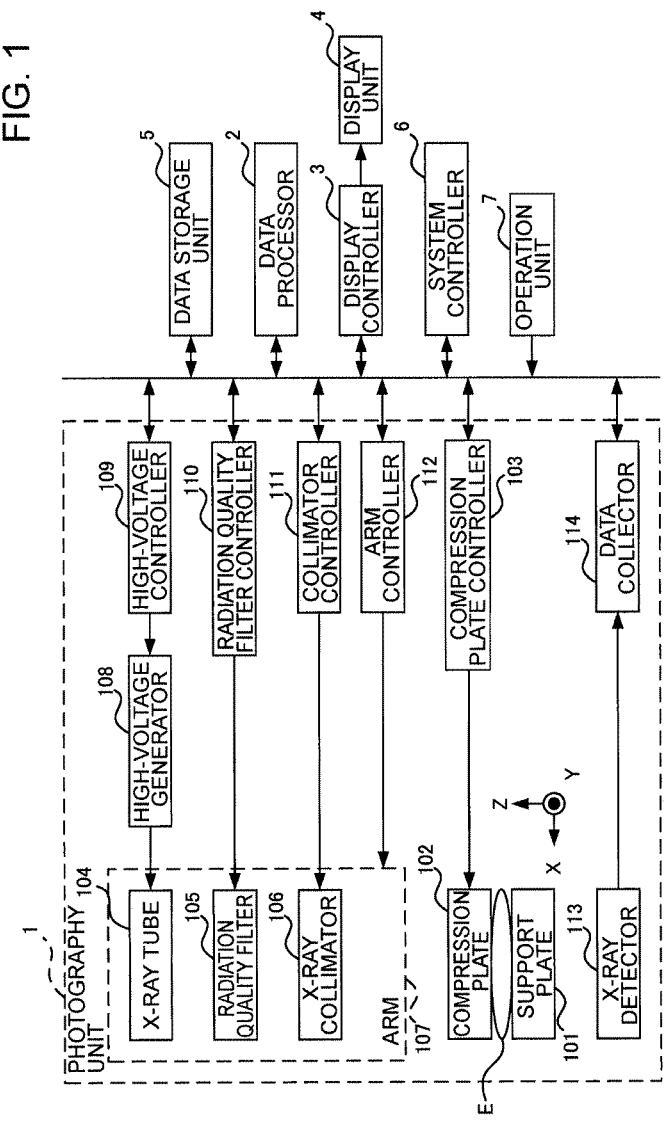
FIG. 1 is a block diagram of a medical image diagnosis apparatus according to an embodiment.

FIG. 1 is a block diagram of a medical image diagnosis apparatus according to an embodiment. The medical image diagnosis apparatus includes a photography unit 1, a data processor 2, a display controller 3, a display unit 4, a data storage unit 5, a system controller 6, and an operation unit 7. In the following, a description is given of the configuration of a mammography apparatus used for imaging a subject E as one example of the medical image diagnosis apparatus of the embodiment. In this embodiment, the subject E is the breast.

(Photography Unit 1)

The photography unit 1 emits radiation to the subject E and detects radiation that has passed through the subject E. The photography unit 1 includes a support plate 101, a compression plate 102, a compression plate controller 103, an X-ray tube 104, a radiation quality filter 105, an X-ray collimator 106, an arm 107, a high-voltage generator 108, a high-voltage controller 109, a radiation quality filter controller 110, a collimator controller 111, an arm controller 112, an X-ray detector 113, and a data collector 114.

(Support Plate 101)

The support plate 101 supports the subject E placed thereon. On the negative Z-direction side of the support plate 101 is located the X-ray detector 113.

(Compression Plate 102)

The compression plate 102 is located opposite the support plate 101. The compression plate 102 is configured to be movable to and away from the support plate 101 (in the positive and negative Z-directions). The compression plate 102 moves under the control of the compression plate controller 103, thereby compressing the subject E.

(Compression Plate Controller 103)

The compression plate controller 103 controls the movement of the compression plate 102 under the control of the system controller 6. With this, the thickness of the subject E compressed by the compression plate 102 is adjusted.

(X-Ray Tube 104)

The X-ray tube 104 is fed with a filament current (tube current) and a high voltage (tube voltage) applied by the high-voltage generator 108 and emits X-rays.

(Radiation Quality Filter 105)

The radiation quality filter 105 is selected under the control of the radiation quality filter controller 110. The radiation quality filter 105 thus selected selectively allows the X-rays generated by the X-ray tube 104 to penetrate therethrough. Specifically, the radiation quality filter 105 allows X-rays with a predetermined energy level to penetrate therethrough. With this, the subject E is irradiated with X-rays with an energy spectrum corresponding to photographing.

(X-Ray Collimator 106)

The X-ray collimator 106 forms a slit (opening), and adjusts the irradiation field of the X-rays that have passed through the radiation quality filter 105 by changing the size and shape of the slit.

(Arm 107)

Figure 2:
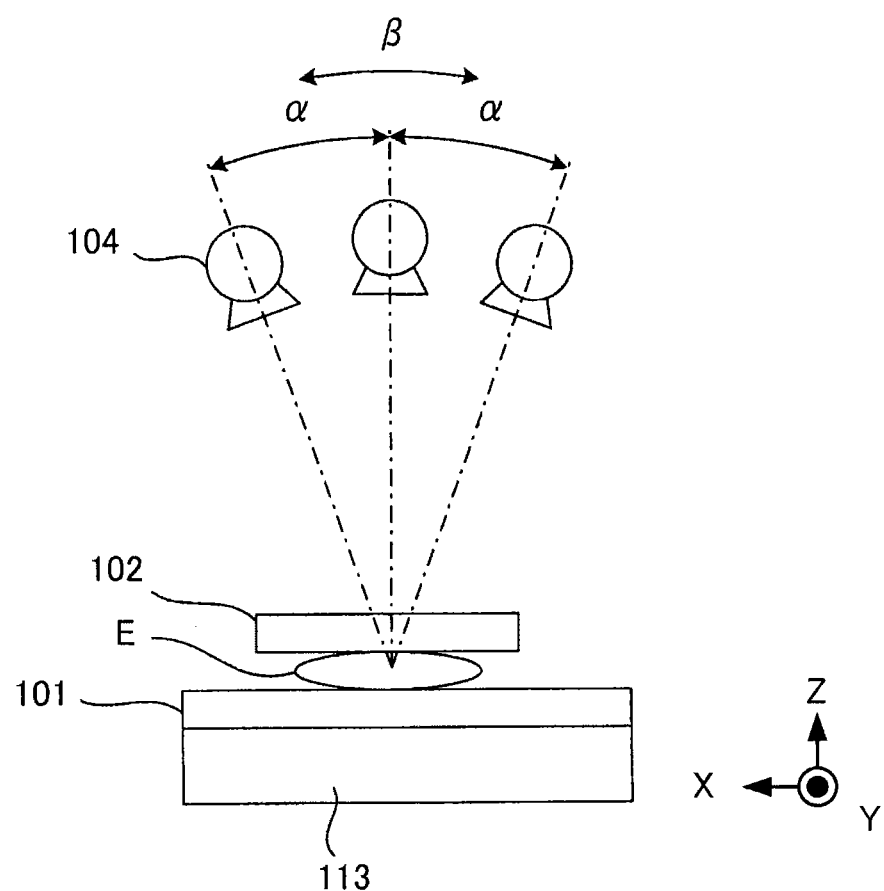
FIG. 2 is a schematic diagram illustrating the movement of an X-ray tube of the embodiment.

The arm 107 moves the X-ray tube 104 with respect to the subject E under the control of the arm controller 112. FIG. 2 is a schematic diagram illustrating the movement of the X-ray tube 104. The arm 107 moves the X-ray tube 104 along a turning direction β from a position (start position) at an angle of α degrees toward one side with respect to the vertical direction of the X-ray detector 113 (positive Z-direction) to a position at an angle of α degrees toward the opposite side.

(High-Voltage Generator 108)

The high-voltage generator 108 applies a high voltage (tube voltage) and feeds a filament current (tube current) to the X-ray tube 104 under the control of the high-voltage controller 109.

(High-Voltage Controller 109)

The high-voltage controller 109 controls the tube voltage and the tube current based respectively on tube voltage conditions and tube current conditions provided from the system controller 6.

(Radiation Quality Filter Controller 110)

The radiation quality filter controller 110 selects the radiation quality filter 105 appropriate to photographing based on radiation quality conditions provided from the system controller 6.

(Collimator Controller 111)

The collimator controller 111 controls the X-ray collimator 106 to adjust the irradiation field according to photographing under the control of the system controller 6.

(Arm Controller 112)

The arm controller 112 turns the arm 107 under the control of the system controller 6. Upon receipt of control information indicating the angle α, the arm controller 112 turns the arm 107 based on the control information. The angle α is determined in advance to be, for example, 15 degrees, 20 degrees, or the like.

(X-Ray Detector 113)

The X-ray detector 113 detects incident X-rays that include those having passed through the subject E. The X-ray detector 113 includes, for example, a direct or indirect conversion flat panel detector. The flat panel detector converts the incident X-rays into electrical signals and outputs them to the data collector 114.

(Data Collector 114)

The data collector 114 performs analog-to-digital (A/D) conversion on the electrical signals received from the X-ray detector 113. The data collector 114 sends digital signals obtained by the conversion to the data processor 2 as detection data.

(Data Processor 2)

Figure 3:
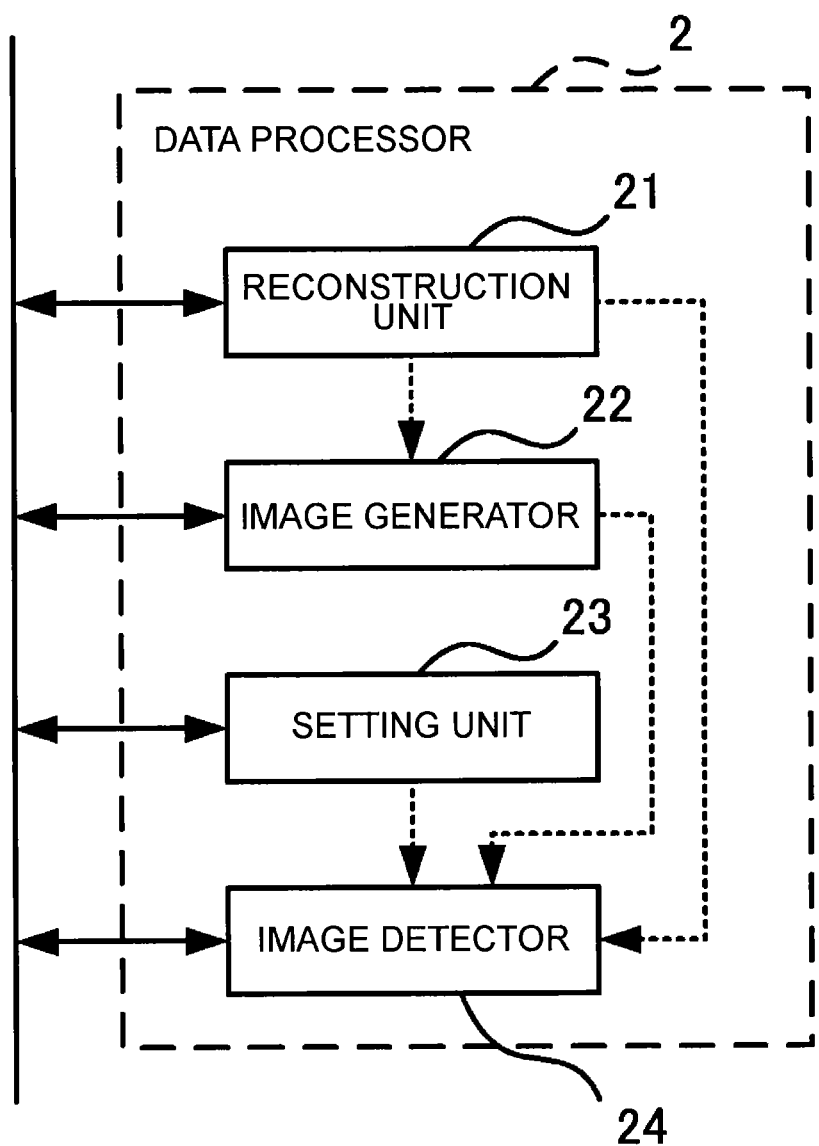
FIG. 3 is a block diagram of a data processor of the embodiment.

The data processor 2 generates 3D image data including a plurality of tomographic images of the subject E based on the detection data from the data collector 114. FIG. 3 is a block diagram of the data processor 2. The data processor 2 includes a reconstruction unit 21, an image generator 22, a setting unit 23, and an image detector 24.

(Reconstruction Unit 21)

The reconstruction unit 21 performs reconstruction such as shift-and-add on the detection data, and generates a plurality of tomographic images of, for example, planes (X-Y planes) perpendicular to the thickness direction of the subject E as the cross-sections. The reconstruction unit 21 stacks the tomographic images to generate 3D image data (tomosynthesis image data). The reconstruction unit 21 outputs the 3D image data to the data storage unit 5. The reconstruction unit 21 may output the 3D image data to the image generator 22.

(Image Generator 22)

The image generator 22 retrieves the 3D image data from the data storage unit 5, and projects it in a predetermined direction to generate a 2D image. The image generator 22 may receive the 3D image data from the reconstruction unit 21.

For example, the predetermined direction is a direction perpendicular to the planes (X-Y planes) of the tomographic images. The predetermined direction is set in advance. The image generator 22 generates a 2D image using the predetermined direction as a projection direction. The image generator 22 projects the pixel value of a pixel having the minimum pixel value that indicates the detection value of radiation detected in the predetermined direction. This corresponds to that the image generator 22 performs minimum intensity projection (MinIP) for the pixel value that indicates the detection value of radiation. At this time, the image generator 22 reads the pixel value of each of a row of pixels, and specifies a pixel having the minimum pixel value that indicates the detection value of radiation from among the row of pixels. The image generator 22 then projects the pixel value of the pixel specified. This corresponds to that the minimum pixel value indicating the detection value of radiation is projected among pixel values of a row of pixels crossed by a projection line in the same direction as the predetermined direction. Thus, the minimum pixel value that indicates the detection value of radiation is specified with respect to each projection line.

Incidentally, the predetermined direction may be the irradiation direction of radiation (X-rays) in a predetermined radiation cone (X-ray cone). For example, the predetermined radiation cone is determined based on the size and shape of the slit formed by the X-ray collimator 106 as well as the angle of the arm 107. In this case, the image generator 22 specifies a pixel having the minimum pixel value that indicates the detection value of radiation with respect to each of projection lines radiating from the focal point of radiation (X-rays).

In general radiography, any of pixels having a small pixel value that indicates the detection value of radiation may represent a lesion. In this case, by the projection of the minimum pixel value that indicates the detection value of radiation, a pixel that is likely to represent a lesion is extracted with respect to each row of pixels of coordinates of a plane perpendicular to the predetermined direction. Note that the value to be projected is not limited to the minimum detection value of radiation, and may be determined in advance as appropriate. For example, the image generator 22 may obtain the average of detection values indicated by a row of pixels, and project the average thus obtained by the average intensity projection (AveIP) to generate pixels of a 2D image.

Figure 4:
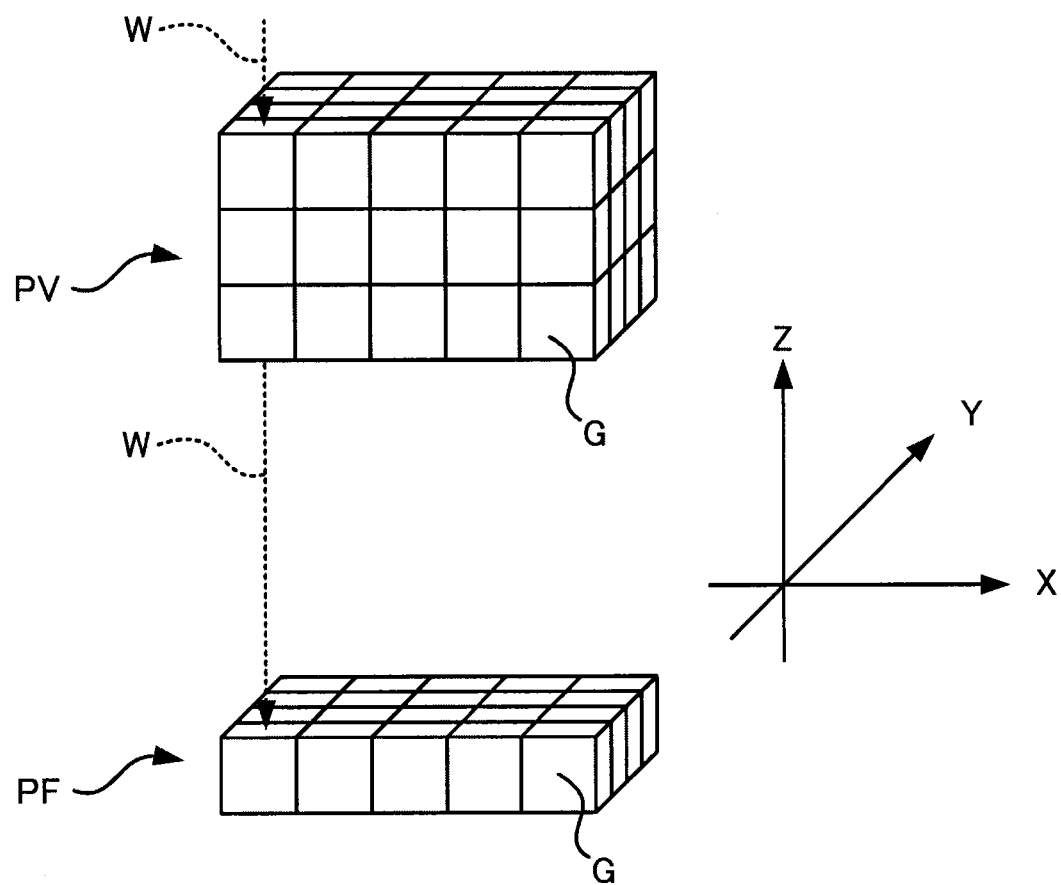
FIG. 4 is a schematic diagram illustrating a relationship between 3D image data and a 2D image in the embodiment.

FIG. 4 is a schematic diagram illustrating a relationship between 3D image data PV and a 2D image PF. A cuboid grid G indicates a pixel in the 3D image data PV and the 2D image PF. Described below is an example in which the predetermined direction W is set to the Z-axis direction. The predetermined direction W corresponds to a projection direction from 3D image data to a 2D image. The image generator 22 projects the pixel value of a pixel having the minimum pixel value that indicates the detection value of radiation in a row of pixels with the same coordinates (X-Y coordinates) of a plane perpendicular to the predetermined direction W from among pixels of the 3D image data. The image generator 22 performs the projection with respect to each row of pixels. With this, the image generator 22 generates the 2D image PF representing an image where the minimum pixel value indicating the detection value of radiation is extracted with respect to each coordinates of a plane perpendicular to the predetermined direction W. The image generator 22 outputs the 2D image PF thus generated to the data storage unit 5. The image generator 22 may output the 2D image PF to the image detector 24.

(Setting Unit 23)

The setting unit 23 sets a region of interest for the 2D image PF. The region of interest refers to a region including a pixel that represents a lesion in the 2D image. For example, the setting unit 23 set the region of interest based on operation information as to the 2D image displayed by the display controller 3 on the display unit 4. While viewing the 2D image, a radiographic interpreter such as a radiologist designates a pixel that represents a lesion by operation on the operation unit 7. Upon receipt of the operation information, the setting unit 23 specifies the coordinates of the pixel thus designated. The setting unit 23 stores a setting range determined in advance, and sets a region in the setting range centered at the coordinates as the region of interest. The radiographic interpreter may perform operation to specify the region including a pixel that represents a lesion. In this case, the setting unit 23 sets the region indicated by the operation information as the region of interest. The setting unit 23 outputs region information indicating the coordinates of the region of interest to the data storage unit 5. The setting unit 23 may output the region information to the image detector 24.

Incidentally, the setting unit 23 may set the region of interest by analyzing the 2D image. For example, the setting unit 23 analyzes the pixel value of the 2D image, and specifies, as a lesion region, a region having pixels with a pixel value indicating the detection value of radiation less than a predetermined threshold in a predetermined range. The setting unit 23 sets a region including the lesion region as the region of interest.

(Image Detector 24)

Based on the region of interest and a corresponding region that corresponds to the region of interest in each tomographic image, the image detector 24 detects a tomographic image including the corresponding region that is similar in pixel value to the region of interest from the 3D image data. The image detector 24 retrieves the 3D image data, the 2D image, and the region information from the data storage unit 5. The image detector 24 may receive the 3D image data, the 2D image, and the region information from the reconstruction unit 21, the image generator 22, and the setting unit 23, respectively.

Figure 5:
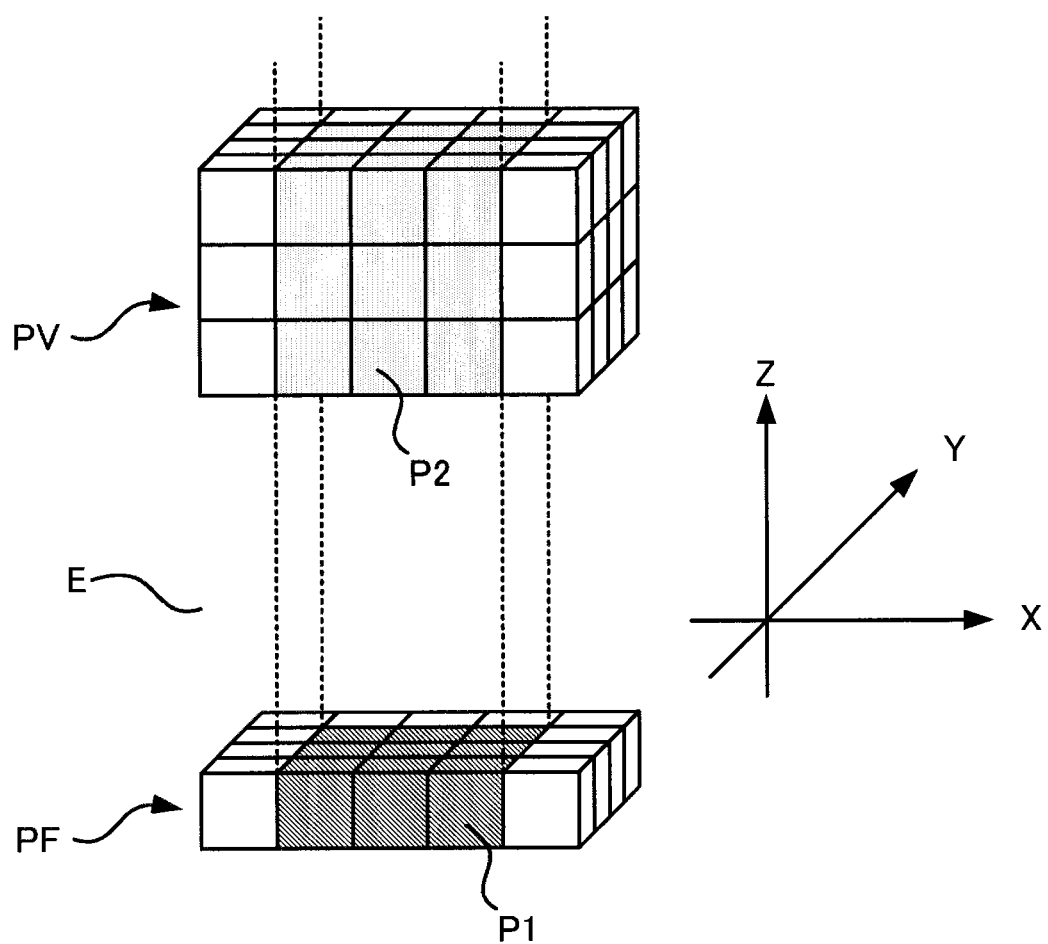
FIG. 5 is a schematic diagram illustrating a relationship between 3D image data and a 2D image where a region of interest is set in the embodiment.

Specifically, the image detector 24 specifies the corresponding region in each tomographic image based on the coordinates of the region of interest and the coordinates of the 3D image data. FIG. 5 is a schematic diagram illustrating a relationship between the 3D image data PV and the 2D image PF where the region of interest is set. Pixels P1 are those included in the region of interest. Pixels P2 are those included in the corresponding region. From the 3D image data, the image detector 24 extracts a group of the pixels P2 with the same 2D coordinates (X-Y coordinates) as the coordinates of the region of interest indicated by the region information. The corresponding region is specified by the image detector 24 as a region of a group of pixels extracted for each of tomographic images with a 2D plane (X-Y plane) as the cross-section.

The image detector 24 generates a difference image that indicates a difference between the pixel value of the region of interest and that of the corresponding region with respect to each of the tomographic images based on the corresponding region specified. The image detector 24 calculates a difference between the pixel value of the pixels P1 indicating the detection value of radiation in the region of interest and that of the pixels P2 indicating the detection value of radiation in the corresponding region with respect to each pair of pixels P1 and P2 with the same 2D coordinates (X-Y coordinates). The image detector 24 arranges pixels having the difference as the pixel value in a 2D plane (X-Y plane) to generate the difference image. The image detector 24 generates the difference image with respect to each sectional position (Z coordinates). With this, the difference image is generated for each tomographic image.

The image detector 24 calculates the standard deviation of pixel values in each difference image. The image detector 24 determines a group of pixels included in the difference image as a general population, and calculates a standard deviation using the pixel value that indicates the detection value of radiation as a standard. The image detector 24 performs this calculation with respect to each difference image. With this, the standard deviation is obtained for each sectional position (Z coordinates).

Figure 6:
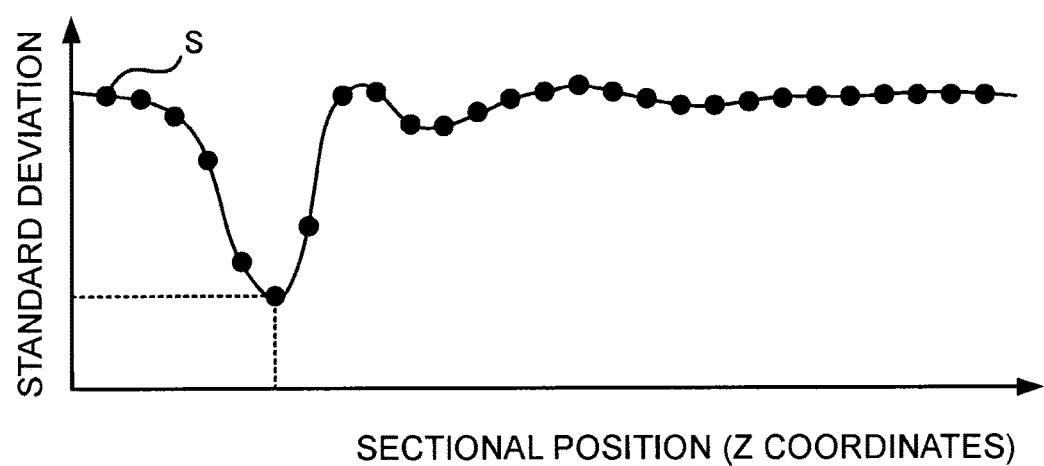
FIG. 6 is a schematic diagram illustrating a relationship between a sectional position and a standard deviation in the embodiment.

The image detector 24 detects a tomographic image of a difference image with the minimum standard deviation as the tomographic image including the corresponding region that is similar in pixel value to the region of interest. FIG. 6 is a schematic diagram illustrating a relationship between a sectional position and a standard deviation. In FIG. 6, the horizontal axis indicates the sectional position (Z coordinates), while the vertical axis indicates the standard deviation. Dots S each indicate the standard deviation with respect to each sectional position (Z coordinates). The image detector 24 specifies a sectional position with the minimum standard deviation from among sectional positions (Z coordinates) where a standard deviation has been calculated. The image detector 24 detects a tomographic image of the sectional position thus specified as the tomographic image including the corresponding region that is similar in pixel value to the region of interest. Thus, the 3D position (X, Y, and Z coordinates) of the corresponding region that is the most similar to an image in the region of interest is three-dimensionally specified. This corresponds to that a desired position (a position desired by a radiographic interpreter such as a radiologist) is three-dimensionally specified.

The closer (more similar) the pixel value of pixels in the corresponding region is to that in the region of interest, the smaller is the pixel value of pixels in the difference image. Besides, the standard deviation is smaller for the difference image of the corresponding region including the larger number of pixels having a pixel value closer to that of pixels in the region of interest. Accordingly, by the detection of a tomographic image of a difference image with the minimum standard deviation as a tomographic image including the corresponding region that is similar in pixel value to the region of interest, the image detector 24 detects a tomographic image that includes the corresponding region having the larger number of pixels with a pixel value closer to that of pixels in a lesion and around the lesion. The image detector 24 outputs the tomographic image thus detected to the data storage unit 5. The image detector 24 may output the tomographic image to the display controller 3.

(Display Controller 3)

Figure 7:
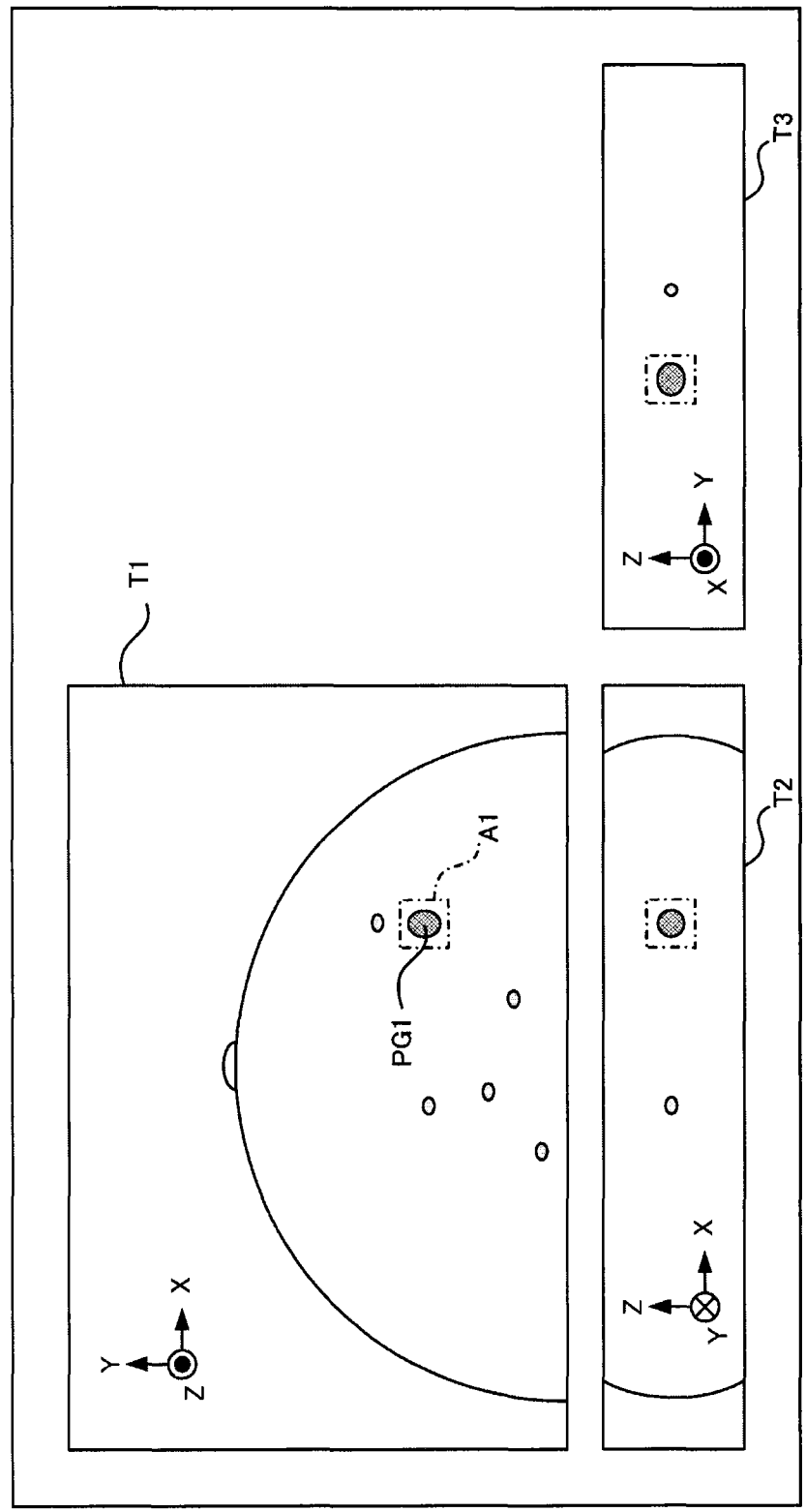
FIG. 7 is a schematic view of an example of display of a tomographic image in the embodiment.

The display controller 3 retrieves the tomographic image detected by the image detector 24 from the data storage unit 5, and displays it on the display unit 4. The display controller 3 may receive the tomographic image from the image detector 24. FIG. 7 is a schematic view of an example of display of the tomographic image. In FIG. 7, a tomographic image T1 is the tomographic image detected by the image detector 24 and includes a corresponding region A1. A pixel group PG1 formed of pixels with the same 2D coordinates (X-Y coordinates) as a lesion specified in a 2D image may represent the lesion in the tomographic image T1.

The display controller 3 may display a tomographic image that includes the center of the corresponding region A1 and that is of a different cross-section than the tomographic image T1 on the display unit 4 together with the tomographic image T1 based on 3D image data. For example, the display controller 3 refers to the center of the corresponding region A1 and the 3D image data stored in the data storage unit 5, and displays a tomographic image T2 of the Z-Y plane as the cross-section and a tomographic image T3 of the Y-X plane as the cross-section on the display unit 4. With this, a radiographic interpreter such as a radiologist can view the lesion in the corresponding region A1 from a plurality of directions.

(Display Unit 4)

The display unit 4 displays the tomographic image under the control of the display controller 3. The display unit 4 includes a display device such as a liquid crystal display (LCD), an organic electro-luminescence (EL) display, or the like.

(Data Storage Unit 5)

The data storage unit 5 stores the 3D image data, the 2D image, the region information, and the tomographic image received from the reconstruction unit 21, the image generator 22, the setting unit 23, and the image detector 24, respectively. The data storage unit 5 includes a storage device such as a hard disk drive (HDD) or the like.

(System Controller 6)

The system controller 6 controls the functions of each unit of the medical image diagnosis apparatus. The system controller 6 includes a processor such as a central processing unit (CPU) and a storage device such as HDD. The system controller 6 stores a computer program for implementing the functions of each unit of the medical image diagnosis apparatus and executes it, thereby implementing the functions.

(Operation Unit 7)

The operation unit 7 is used to input various types of instructions and information to the medical image diagnosis apparatus. The operation unit 7 includes operation devices such as a keyboard, a mouse, a foot pedal, and the like. The operation unit 7 may include a graphical user interface (GUI) displayed in the display unit 4.

[Operation]

Figure 8:
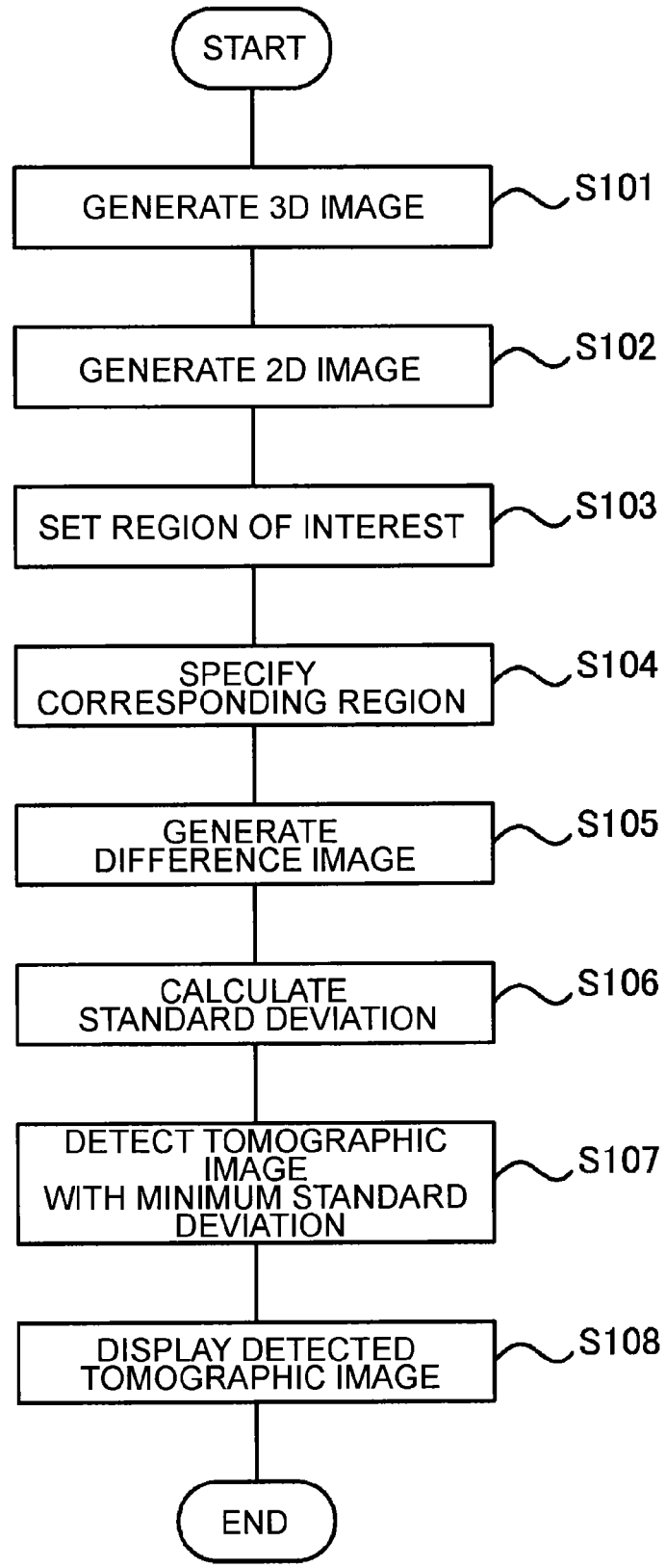
FIG. 8 is a flowchart of the operation of the medical image diagnosis apparatus of the embodiment.

FIG. 8 is a flowchart of the operation of the medical image diagnosis apparatus of the embodiment.

(Step S101)

The photography unit 1 emits radiation to the subject E and detects radiation that has passed through the subject E. On this occasion, the photography unit 1 detects radiation that has passed through the subject E at different angles with respect to the subject E while moving the X-ray tube 104 (tomosynthesis imaging). The reconstruction unit 21 performs reconstruction such as shift-and-add on the detection data, and generates a plurality of tomographic images of planes (X-Y planes) perpendicular to the thickness direction of the subject E as the cross-sections. The reconstruction unit 21 stacks the tomographic images and thereby generates 3D image data. The reconstruction unit 21 outputs the 3D image data to the data storage unit 5.

(Step S102)

The image generator 22 retrieves the 3D image data from the data storage unit 5. The image generator 22 projects the 3D image data in a predetermined direction and thereby generates a 2D image. The image generator 22 outputs the 2D image to the data storage unit 5.

(Step S103)

The setting unit 23 sets a region of interest for the 2D image. For example, having received operation information corresponding to operation for designating a pixel performed on the operation unit 7 by a radiographic interpreter such as a radiologist, the setting unit 23 specifies the coordinates of the pixel designated. The setting unit 23 sets a region in the setting range centered at the coordinates as the region of interest. The setting unit 23 outputs region information indicating the coordinates of the region of interest to the data storage unit 5.

(Step S104)

The image detector 24 retrieves the 3D image data, the 2D image, and the region information from the data storage unit 5. The image detector 24 specifies a corresponding region in each tomographic image based on the coordinates of the region of interest and the coordinates of the 3D image data.

(Step S105)

The image detector 24 generates a difference image that indicates a difference between the pixel value of the region of interest and that of the corresponding region with respect to each tomographic image based on the corresponding region specified.
(Step S106)

The image detector 24 calculates the standard deviation of pixel values in each difference image. The image detector 24 determines a group of pixels included in the difference image as a general population, and calculates a standard deviation using the pixel value that indicates the detection value of radiation as a standard.
(Step S107)

The image detector 24 detects a tomographic image of a difference image with the minimum standard deviation as a tomographic image including the corresponding region that is similar in pixel value to the region of interest. The image detector 24 outputs the tomographic image thus detected to the data storage unit 5.
(Step S108)

The display controller 3 retrieves the tomographic image detected by the image detector 24 from the data storage unit 5, and displays it on the display unit 4.

According to the embodiment, the medical image diagnosis apparatus emits radiation to the subject E and detects radiation that has passed through the subject E, thereby generating 3D image data including a plurality of tomographic images of the subject E. The medical image diagnosis apparatus includes the image generator 22, the setting unit 23, the image detector 24, and the display controller 3. The image generator 22 projects the 3D image data in a predetermined direction and thereby generates a 2D image. The setting unit 23 sets a region of interest for the 2D image. Based on the region of interest and a corresponding region that corresponds to the region of interest in each tomographic image, the image detector 24 detects a tomographic image including the corresponding region that is similar in pixel value to the region of interest from the 3D image data. The display controller 3 displays the tomographic image detected by the image detector 24 on the display unit 4. In this manner, the medical image diagnosis apparatus of this embodiment detects a tomographic image including a corresponding region that is similar to a region of interest set in a 2D image based on 3D image data. As described above, the medical image diagnosis apparatus generates a 2D image on which a pixel that may represent a lesion has been projected. This facilitates the detection of even a lesion that overlaps with the mammary gland in the thickness direction of the breast. Besides, the medical image diagnosis apparatus sets a region of interest in the 2D image, and detects a tomographic image including a region that is similar to the region of interest. This eliminates the need for searching for a lesion while tomographic images are switched from one to another on the display. Thus, the medical image diagnosis apparatus facilitates the detection of a lesion in 3D image data.

Besides, the medical image diagnosis apparatus of this embodiment generates a 2D image based on 3D image data. This reduces variance in detection accuracy due to a difference in noise between the 2D image and the 3D image data. Thus, the medical image diagnosis apparatus is capable of detecting a lesion in the 3D image data with a high degree of accuracy.

In addition, since the 2D image is generated based on the 3D image data, radiation exposure can be reduced compared to a conventional method that requires to capture a 2D image. Accordingly, the medical image diagnosis apparatus is capable of detecting a lesion in the 3D image data while reducing the radiation exposure of the subject E.

While a mammography apparatus is described as an example of the medical image diagnosis apparatus of the embodiment, the embodiment may be applicable to any other medical image diagnosis apparatuses capable of generating 3D image data such as general chest X-ray equipment.
(Modification)

The medical image diagnosis apparatus of this modification is different from that of the above embodiment in the configuration of the image detector 24 and the display controller 3. In the following, the difference is mainly described.

As well as detecting a tomographic image including a corresponding region that is similar in pixel value to a region of interest from 3D image data, the image detector 24 detects a predetermined number of other tomographic images in order of similarity in pixel value to the region of interest. The number of tomographic images detected by the image detector 24 is determined in advance. The image detector 24 outputs a group of the tomographic images thus detected to the data storage unit 5. The image detector 24 may output the group of the tomographic images to the display controller 3.

The display controller 3 retrieves the group of the tomographic images detected by the image detector 24 from the data storage unit 5. Together with the tomographic image including a corresponding region that is most similar in pixel value to the region of interest, the display controller 3 displays the other tomographic images arranged in order of similarity in pixel value to the region of interest on the display unit 4. The display controller 3 may receive the group of the tomographic images from the image detector 24.

Figure 9:
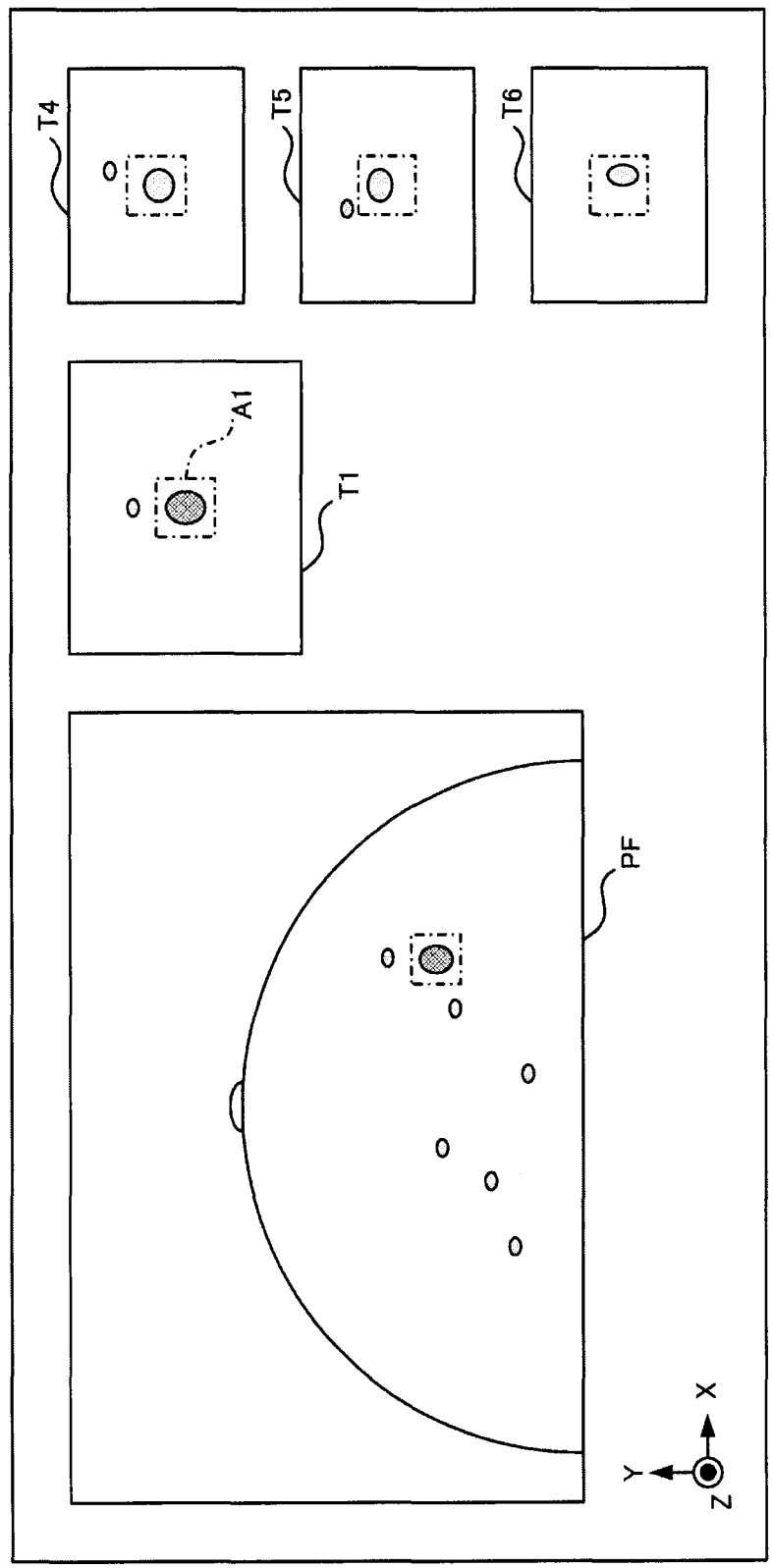
FIG. 9 is a schematic view of an example of display of a group of tomographic images in a modification of the embodiment.

FIG. 9 is a schematic view of an example of display of a group of tomographic images. In FIG. 9, together with the tomographic image T1 including a corresponding region that is most similar in pixel value to a region of interest detected by the image detector 24, other tomographic images T4, T5, and T6 are displayed in an arrangement. The display layout of the tomographic images T1, T4, T5, and T6 can be determined as appropriate. The display controller 3 may display the 2D image PF arranged with the tomographic images.

Similarly, in addition to detecting a tomographic image including a corresponding region that is similar in pixel value to a region of interest from 3D image data, the image detector 24 may detect a predetermined number of other tomographic images in sectional positions near the tomographic image. In this case, together with the tomographic image including a corresponding region that is most similar to the region of interest, the display controller 3 displays the other tomographic images in an arrangement on the display unit 4.

According to the modification, together with a tomographic image including a corresponding region that is most similar in pixel value to a region of interest, the medical image diagnosis apparatus displays other tomographic images in order of similarity in pixel value to the region of interest. This means that a plurality of tomographic images are displayed in order of likelihood of demonstrating a lesion. With this, a radiographic interpreter such as a radiologist can view a plurality of tomographic images that are highly likely to demonstrate a lesion.

Further, according to the modification, together with a tomographic image including a corresponding region that is most similar to a region of interest, the medical image diagnosis apparatus may display other tomographic images in sectional positions near the tomographic image. This means that, together with a tomographic image that is highly likely to demonstrate a lesion, those near the tomographic image are displayed as well. Thus, a radiographic interpreter such as a radiologist can view an image at a position highly likely to demonstrate a lesion and also images of cross-sections near the position.

As described above, according to the embodiment and the modification thereof, the medical image diagnosis apparatus detects a tomographic image including a corresponding region that is similar to a region of interest set in a 2D image based on 3D image data. Thus, the medical image diagnosis apparatus is capable of detecting a lesion in the 3D image data while reducing the radiation exposure of a subject.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus configured to emit radiation to a breast as a subject, detect radiation that has passed through the subject, and generate three-dimensional image data including a plurality of tomographic images of the subject, the medical image diagnosis apparatus comprising:
    an image generator configured to project a pixel value of a pixel, of the three-dimensional image data, having a minimum pixel value that indicates a detection value of the radiation detected in a predetermined direction that is perpendicular to planes of the tomographic images to generate a two-dimensional image;
    a setting unit configured to set a region of interest in the two-dimensional image;
    an image detector configured to detect, based on the region of interest and a corresponding region that corresponds to the region of interest in each of the tomographic images, a tomographic image including the corresponding region that is similar in pixel value to the region of interest from the three-dimensional image data; and
    a display controller configured to display the tomographic image detected by the image detector on a display unit.

2. The medical image diagnosis apparatus of claim 1, wherein the display controller is configured to display, together with the tomographic image detected by the image detector, other tomographic images arranged in order of similarity in pixel value to the region of interest on the display unit.

3. The medical image diagnosis apparatus of claim 1, wherein the display controller is configured to display, together with the tomographic image detected by the image detector, a predetermined number of other tomographic images in sectional positions near the tomographic image.

4. A medical image diagnosis apparatus configured to emit radiation to a breast as a subject, detect radiation that has passed through the subject, and generate three-dimensional image data including a plurality of tomographic images of the subject, the medical image diagnosis apparatus comprising:
    an image generator configured to project a pixel value of a pixel, of the three-dimensional image data, having a minimum pixel value that indicates a detection value of the radiation detected in a predetermined direction in which the radiation is emitted in a predetermined radiation cone to generate a two-dimensional image;
    a setting unit configured to set a region of interest in the two-dimensional image;
    an image detector configured to detect, based on the region of interest and a corresponding region that corresponds to the region of interest in each of the tomographic images, a tomographic image including the corresponding region that is similar in pixel value to the region of interest from the three-dimensional image data; and
    a display controller configured to display the tomographic image detected by the image detector on a display unit.

5. The medical image diagnosis apparatus of claim 4, wherein the display controller is configured to display, together with the tomographic image detected by the image detector, other tomographic images arranged in order of similarity in pixel value to the region of interest on the display unit.

6. The medical image diagnosis apparatus of claim 4, wherein the display controller is configured to display, together with the tomographic image detected by the image detector, a predetermined number of other tomographic images in sectional positions near the tomographic image.

7. A medical image diagnosis apparatus configured to emit radiation to a breast as a subject, detect radiation that has passed through the subject, and generate three-dimensional image data including a plurality of tomographic images of the subject, the medical image diagnosis apparatus comprising:
    an image generator configured to project the three-dimensional image data in a predetermined direction to generate a two-dimensional image;
    a setting unit configured to set a region of interest in the two-dimensional image;
    an image detector configured to generate a difference image that indicates a difference in pixel value between the region of interest and a corresponding region with respect to each of the tomographic images, to calculate a standard deviation of pixel values in the difference image in each of the difference image, and to detect, based on the region of interest and the corresponding region that corresponds to the region of interest in each of the tomographic images, a tomographic image of the difference image with a minimum standard deviation, including the corresponding region that is similar in pixel value to the region of interest from the three-dimensional image data; and
    a display controller configured to display the tomographic image detected by the image detector on a display unit.

8. The medical image diagnosis apparatus of claim 7, wherein the display controller is configured to display, together with the tomographic image detected by the image detector, other tomographic images arranged in order of similarity in pixel value to the region of interest on the display unit.

9. The medical image diagnosis apparatus of claim 7, wherein the display controller is configured to display, together with the tomographic image detected by the image detector, a predetermined number of other tomographic images in sectional positions near the tomographic image.

* * * * *